United States Patent [19]
Reynolds et al.

[11] Patent Number: 6,110,683
[45] Date of Patent: Aug. 29, 2000

[54] AUTOMATED DNA SEQUENCER LOADING DYE WHICH CONTAINS A LANE TRACKING AID

[75] Inventors: Thomas R. Reynolds, Midlothian; Gregory A. Meyers; Gregory A. Buck, both of Richmond, all of Va.; Joshua Rameaka, Durham, N.C.

[73] Assignee: Commonwealth Biotechnologies, Inc., Richmond, Va.

[21] Appl. No.: 09/239,826

[22] Filed: Jan. 29, 1999

Related U.S. Application Data

[63] Continuation of application No. 09/227,576, Jan. 8, 1999.
[51] Int. Cl.$^7$ ..................................................... C12Q 1/68
[52] U.S. Cl. ............................ 435/6; 435/91.1; 436/501; 536/22.1; 536/25.3
[58] Field of Search ..................... 435/6, 91.1; 436/501; 536/25.3, 22.1

[56] References Cited

U.S. PATENT DOCUMENTS

| | | | |
|---|---|---|---|
| 5,658,751 | 8/1997 | Yue et al. ................................... | 435/34 |
| 6,013,444 | 1/2000 | Dau et al. .................................... | 435/6 |

OTHER PUBLICATIONS

Sanger, et al., "DNA Sequencing With Chain–Terminating Inhibitors", *Proc. Natl. Acad. Sci. USA* 74:5463–5467 (1977).
Kaiser, et al "Specific–Primer–Directed DNA Sequencing Using Automated Fluorescence Detection", *Nucl. Acids. Res.* 17(15):6087–6102 (1989).
Hunkapillar et al, "Large–Scale and Automated DNA Sequence Determination", *Science* 254(5028):59–67 (1991).

*Primary Examiner*—Ardin H. Marschel
*Attorney, Agent, or Firm*—Burns, Doane, Swecker & Mathis, L.L.P.

[57] ABSTRACT

The present invention provides a reagent which can be used as a marker to identify individual lanes on an electrophoresis gel which is run on an Automated DNA Sequencer. This reagent is may be included in the loading dye for samples in DNA sequencing, DNA fragment analysis, or linkage mapping analysis. Inclusion of the reagent aids in the identification of the lane in which each sample is individually loaded on the acrylamide gel, such that the data read from each lane by the instrument is correctly applied to the appropriate sample.

63 Claims, 8 Drawing Sheets

(7 of 8 Drawing Sheet(s) Filed in Color)

---

FORMULATION OF LANE TRACKING DYE

5'-(6-FAM) *TAATACGACTCACTATAG-3' 18 Base Oligo
concentration of 1 mg/mL

↓ final concentration of 0.01 nanograms/μl

Mix Containing 5:1 ratio of Dionized Foramide (5 parts)
and 50 mg/mL Blue Dextran (1 part)

FORMULATION OF LANE TRACKING DYE

5'-(6-FAM) *TAATACGACTCACTATAG-3' 18 Base Oligo
concentration of 1 mg/mL final concentration of
0.01 nanograms/µl Mix Containing 5:1 ratio of Dionized Foramide (5 parts)
and 50 mg/mL Blue Dextran (1 part)

US 6,110,683

SEQUENCE LISTING

<160> NUMBER OF SEQ ID NOS: 1

<210> SEQ ID NO 1
<211> LENGTH: 19
<212> TYPE: DNA
<213> ORGANISM: A reagent used as a marker

<400> SEQUENCE: 1
taatacgact cactattag                                              19

AUTOMATED DNA SEQUENCER LOADING DYE WHICH CONTAINS A LANE TRACKING AID

This application claims priority under 35 U.S.C. §§119 and/or 365 to Reynolds et al., U.S. patent application Ser. No. 09/227,576; filed on Jan. 8, 1999; the entire contents of which is hereby incorporated by reference.

BACKGROUND OF THE INVENTION

1. Field of the Invention

We herein describe the formulation of a reagent which can be used as a marker to identify individual lanes on an electrophoresis gel which is run on an Automated DNA Sequencer. This reagent is intended to be included in the loading dye for samples in at least the following applications: DNA sequencing, genetic fragment analysis, linkage mapping analysis, human DNA identity testing, animal DNA identity testing, and DNA paternity testing. Inclusion of the reagent aids in the identification of the lane in which each sample is individually loaded on the acrylamide gel, such that the data read from each lane by the instrument is correctly applied to the appropriate sample. Specifically, this invention is the formulation of a fluorescent dye label attached to a synthetic DNA molecule (oligonucleotide) which has been constituted in a loading buffer. The invention will facilitate manual lane tracking of all samples loaded on an automated DNA sequencer acrylamide gel. With the appropriate modifications to the existing software, he invention will facilitate automated lane tracking on DNA sequencer acrylamide gels.

2. Description of the Related Art

Development of rapid and sensitive nucleic acid sequencing methods utilizing automated fluorescence detection strategies has revolutionized modern molecular biology (see, e.g., Sanger, F., S. Nicklen, A. R. Coulson (1977) *Proc. Natl. Acad. Sci. USA* 74:5463–5467; Kaiser, R. J., et al. (1989) *Nucl. Acids. Res.* 17(15):6087–6102; Hunkapillar, T. et al. (1991) *Science* 254(5028):59–67). Analysis of entire genomes of plants, fungi, animals, bacteria, and viruses is now possible. To keep pace with the huge volume of data required to decipher the genome of any particular organism, modern sequencing instruments have been developed which allow for high throughput sample analysis while automating sample handing and data analysis. However, there continue to be technical problems for accurate sample identification throughout the sequencing process.

One technical problem which hinders sequence analysis of DNA is the inability of the investigator or the DNA sequencer to accurately monitor sample application "lanes" on DNA sequencing acrylamide gels. For example, it is not at all uncommon for samples which have been reconstituted with the standard loading dye formulation to contain no fluorescent components (due to failures of the sequencing reaction chemistries) or to contain only moderately fluorescent sequencing components, due to partial failures of the sequencing reaction chemistries.

Prior to applying the samples to the lanes of a sequencing acrylamide gel, however, the investigator has no idea whether a particular sample reaction has been successful. Imagine, then, that some unsuccessful reaction samples are loaded in the midst of successful reaction samples across 96 lanes of a sequencing gel. As a consequence, improper lane assignments (called tracking) are often made because the automated sequencer fails to mark (i.e., skips) lanes which do not contain fluorescent components. This critical mistake often leads to improper lane assignments which in turn often adversely affects al subsequent data analysis, including misinterpretation of the DNA sequence of the sample under study.

Accordingly, it is clear that there exists a need in the art for proper lane identification and assignment, regardless of the success outcome of the sequencing chemistry reaction. Use of such a method would inevitably improve the results of high throughput screening DNA sequence analysis.

SUMMARY OF THE INVENTION

Briefly, the present invention provides a reagent which can be used as a marker to identify individual lanes on an electrophoresis gel run on an automated DNA sequencer. The reagent is formulated by mixing the standard loading dye to used on automated DNA sequencers with a synthetic oligonucleotide ("oligo") which has been synthesized so as to contain a fluorophore at its 5'-end.

The reagent is intended to be used in a manner such that the fluorogenic oligo is included in the loading dye formulation for each sample for every lane to be run on the acrylamide gel. Therefore, regardless of the success of a sequencing reaction, every lane will contain a fluorophore which can be readily detected by the automated sequencer, and the operator will be able to accurately assign all lanes of the gel.

The reagent is suitable for inclusion in the loading buffers for samples in at least the following applications: DNA sequencing, genetic fragment analysis, linkage mapping, human DNA identity testing, animal DNA identity testing, and DNA paternity testing.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Figure 1:
FIG. 1 illustrates the formulation of the reagent.

(A) A DNA sequencing gel in which the samples were constituted in loading dye which contained the fluorescent oligo of the present invention.

(B) the identical gel, showing the alignment of the instrument's cursor through all the lanes.

(C) A DNA sequencing gel file in which the identical samples run in (A) were constituted in loading dye which DID NOT contain the fluorogenic oligo.

(D) An enlargement of the region for sample Lanes 1–20 which illustrates the use of the fluorogenic oligo.

FIGS. 3A–3C:

(A) A DNA sequencing gel file in which the samples were constituted in loading dye which contained the fluorogenic oligo of the present invention.

(B) A DNA sequencing gel file in which the identical samples in (A) were constituted in loading dye which DID NOT contain the fluorogenic oligo.

(C) an enlargement of the region for sample Lanes 12–33 which illustrates use of the fluorogenic oligo.

DETAILED DESCRIPTION OF THE PREFERRED EMBODIMENTS OF THE INVENTION

The present invention provides a reagent which can be used as a marker to identify individual lanes on an electrophoresis gel run on an automated DNA sequencer. The reagent is suitable for inclusion in the loading buffers for samples in at least the following applications: DNA sequencing, genetic fragment analysis, linkage mapping, human DNA identity testing, animal DNA identity testing, and DNA paternity testing. The reagent is formulated by mixing the standard loading dye used on automated DNA sequencers (typically a 5:1 ratio of deionized formamide and 50 mg/ml blue dextran in 25 mM EDTA, pH 8.0), with a DNA fragment labeled with a fluorophore. In a preferred embodiment, the labeled DNA fragment is a synthetic oligonucleotide ("oligo") which has been synthesized so as to contain a fluorophore at its 5'-end.

The reagent of the present invention is intended to be used in a manner such that the fluorogenic DNA fragment is included in the loading dye formulation for each sample for every lane to be run on the acrylamide gel. Therefore, regardless of the success of a sequencing reaction, every lane will contain a fluorophore which can be readily detected by the automated sequencer, and the operator will be able to accurately assign all lanes of the gel.

Virtually any fluorophore which can be covalently attached to a DNA fragment can be used in the practice of the present invention. Many fluorophores suitable for labeling DNA are known in the art; for example, see U.S. Pat. No. 5,800,992 to Fodor et al., the contents of which are incorporated herein by reference. The fluorophore should possess a high quantum yield for fluorescence, well-resolved absorption and emission maxima, and cause minimal alteration in the electrophoretic mobility of the DNA to which it is attached. Moreover, it is critical that the fluor be detectable by the DNA sequencer used; one of ordinary skill in the art will readily be able to identify a suitable fluor for use with a particular DNA sequencer. For most DNA sequencers presently in common use, this means that the fluor will preferably emit in the 500–700 nm wavelength range. In a particularly preferred embodiment, the fluorescent moiety used to label the DNA fragment is 6-FAM (6-carboxyfluorescein).

In an alternative embodiment of the present invention, the fluor is selected to have an emission maximum different than any of the four nucleotide dyes, but still within the range of wavelengths characteristic of the instrument in use (as noted above, typically 500–700 nm). Therefore, the tracker would be seen by the sequencer but because of where its emission maximum exists it would not be called as data. The tracking dye can then exist anywhere on the gel, even in the midst of data. Thus, oligos of any size can be used with this approach. One of ordinary skill in the art will readily be able to select a fluorophore appropriate for use with a particular detection instrument from those known in the art.

For use in the present invention, a DNA fragment of any sequence or composition or chain length can be used. In a preferred embodiment, the DNA fragment will be a chemically synthesized oligo, or a DNA fragment amplified by the method of polymerase chain reaction ("PCR"). The oligo is preferably synthesized by automated DNA synthesis protocols using standard phosphoramidite chemistry. The sequence of the DNA is not important and can be of any composition.

In a preferred embodiment of the present invention, the length of the DNA fragment will be selected such that the labeled DNA fragment will enter the acrylamide gel to a migration distance slightly longer than the migration distance of the first set of "real" sequencing data from the sequencing reaction; inclusion of the marker DNA thus does not obstruct, interfere with, or obscure any of the real sequencing data. In a particularly preferred embodiment, oligos with chain length of 17–24 bases are used. This embodiment is particularly suitable for use with chain-termination sequencing strategies. In most cases, DNA fragments of 17–24 bases will enter the acrylamide gel to a migration distance slightly longer than the migration distance of the first set of "real data" of the sequencing reaction. In a particularly preferred embodiment, the DNA fragment is a synthetic oligo 18 bases in length with a nucleotide sequence consisting of TAATACGACTCACTATAG (SEQ ID NO: 1) (the so-called "standard T7 primer").

In an alternative embodiment of the present invention, oligos with a chain length of up to 45 bases are used. This embodiment is particularly suitable for use with primer-based sequencing strategies. For use in this embodiment of the invention, the oligo will optimally be 39 bases in length.

The reagent according to the present invention is preferably prepared according to the following procedure (see FIG. 1). First, deionized formamide and 50 mg/ml blue dextran in 25 mM EDTA, pH 8.0 are mixed in a ratio of 5 parts to 1. Then, 0.01 nanograms (ng) per microliter ($\mu$l) of the selected oligo, to which a fluorophore has been covalently attached, is added.

The following examples are presented in order to more fully illustrate the preferred embodiments of the invention. They should in no way be construed, however, as limiting the broad scope of the invention.

EXAMPLE 1

The reagent according to the present invention was prepared as follows (see FIG. 1):

1. In a ratio of 5 parts to 1, deionized formamide and 50 mg/ml blue dextran were mixed in 25 mM EDTA, pH 8.0

2. To the formulation of step 1 was added 0.01 nanograms (ng) per microliter ($\mu$l) synthetic oligo 18 bases in length of the DNA sequence TAATACGACTCACTATAG (SEQ ID NO: 1) (the so-called "standard T7 primer"), which had been made fluorogenic by incorporation of 6-FAM at the 5'-end of the oligo. The oligo was synthesized by automated DNA synthesis protocols using standard phosphoramidite chemistry.

EXAMPLE 2

Figure 2A:
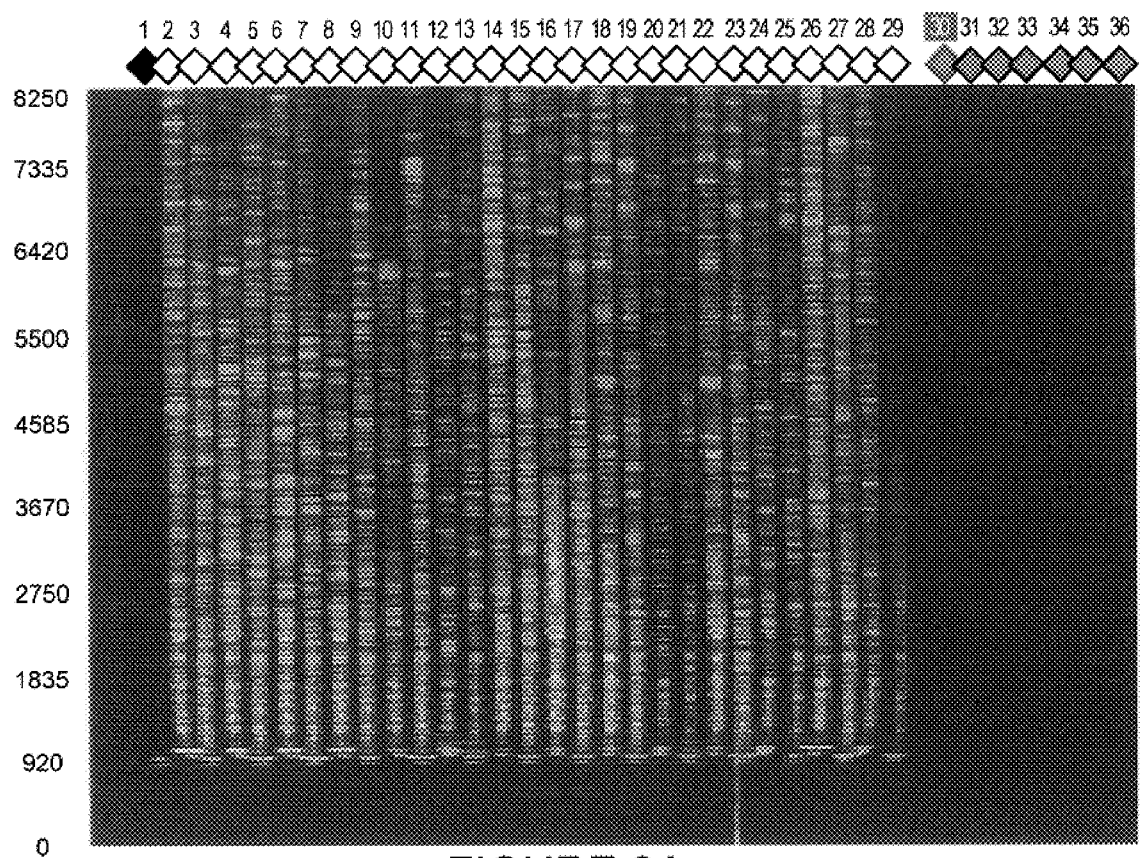
FIGS. 2A–2D.
Figure 2B:
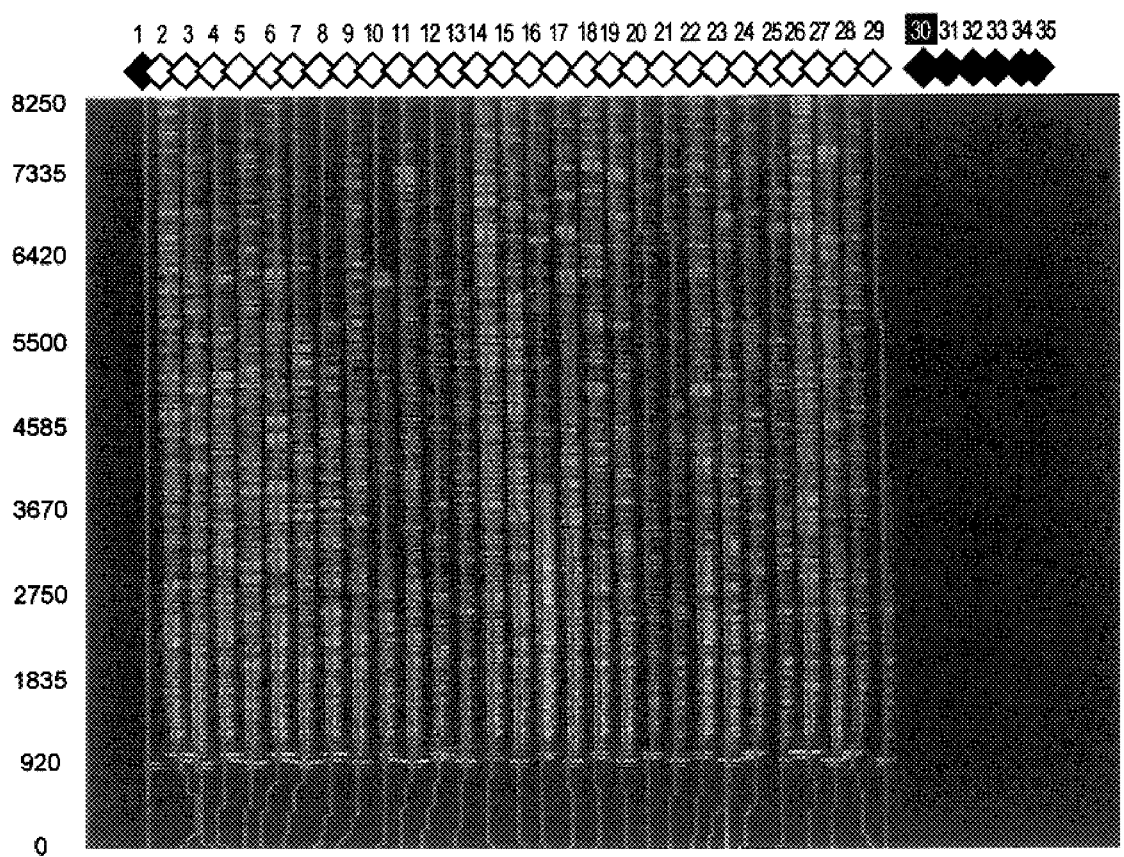
Figure 2C:
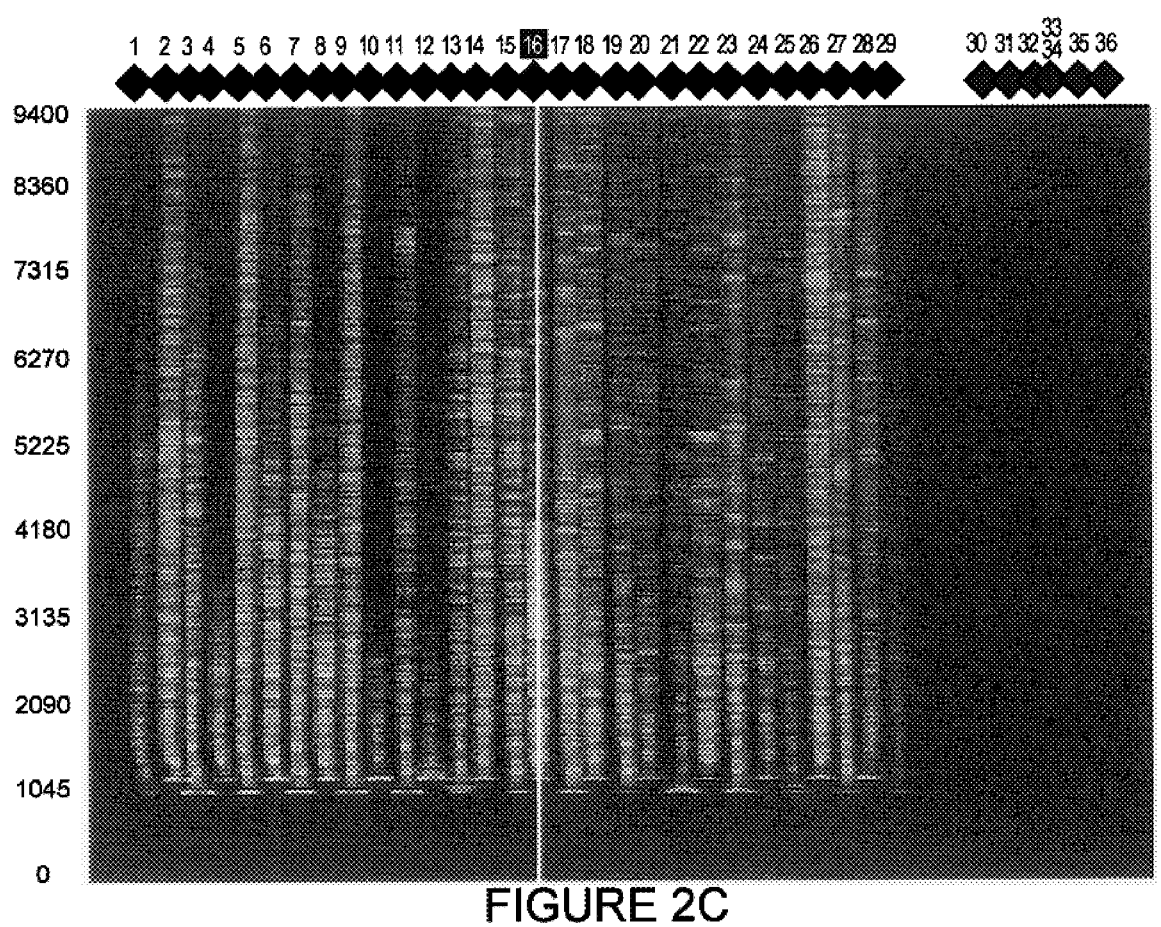
Figure 2D:
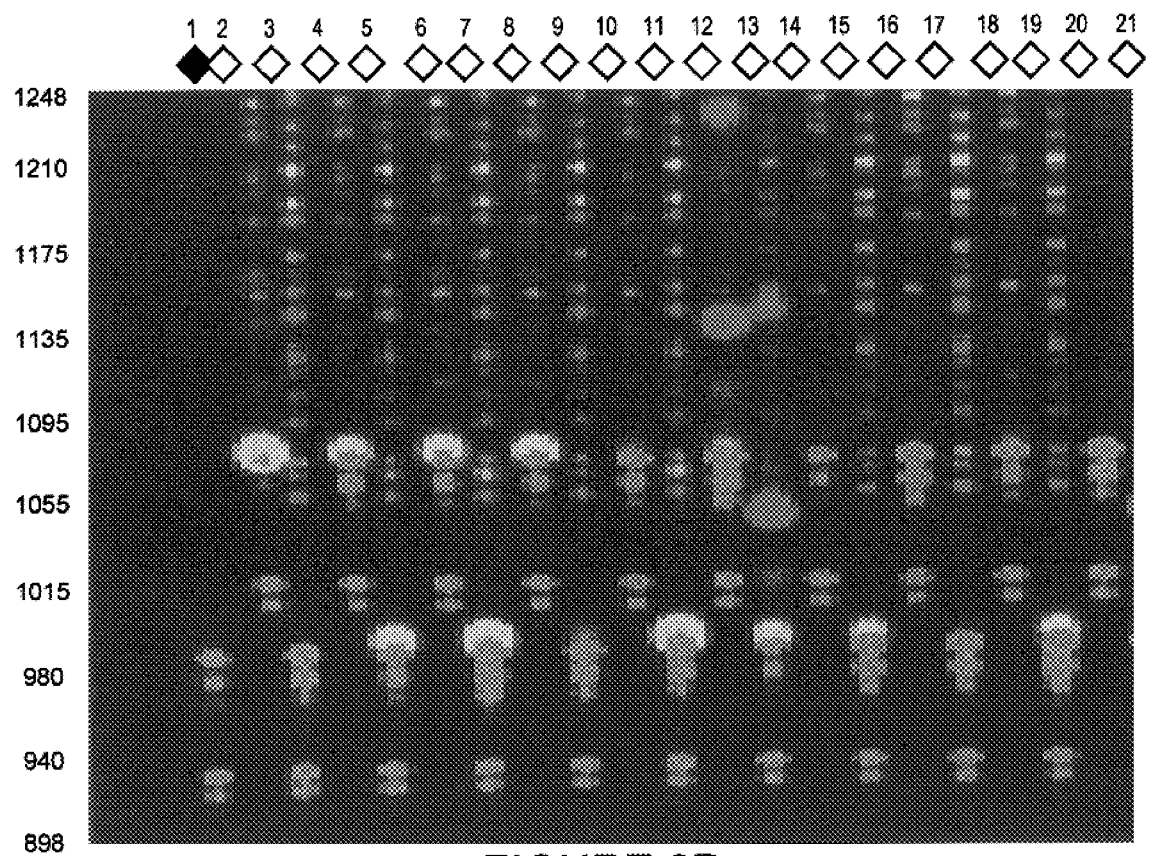

A DNA sequencing gel from a PE Applied Biosystems Model 377 XL Automated DNA sequencer in which the samples were constituted in loading dye which contained the fluorescent oligo of the present invention is shown in FIG. 2A. Each of the twenty-nine lanes on the gel are clearly delineated by the "blue" oligo (at position 920 on the ordinate), and the sequencer had no problem in correctly assigning lane positions. Note that lane 1 is delineated but does NOT contain successful sequencing reaction, and is otherwise blank, except for the presence of the blue oligo. FIG. 2B shows the identical gel, indicating the alignment of the instrument's cursor through all the lanes. Note the correct alignment of the instrument's cursor through Lane 1 because it "found" the blue oligo. FIG. 2C displays the DNA sequencing gel file from a PE Applied Biosystems Model 377 XL Automated DNA sequencer in which the identical samples run above and shown in FIG. 2A were constituted in loading dye which DID NOT contain the fluorogenic oligo. Note that the sequencer INCORRECTLY assigned the reaction in lane 2 as being in lane 1, because it could not "find" the reaction components from Lane 1. An enlargement of the region for sample Lanes 1–20 which illustrates the use of the fluorogenic oligo is shown in FIG. 2D. Note that in the enlargement, the dyed oligo actually runs as a set of four bands in each lane, likely due to different structural conformations assumed by the oligo. Samples in odd numbered lanes are loaded and run for 5 minutes prior to loading samples into even numbered lanes. Hence, the "staggered" appearance to the movement of the fluorogenic oligo.

EXAMPLE 3

Figure 3A:
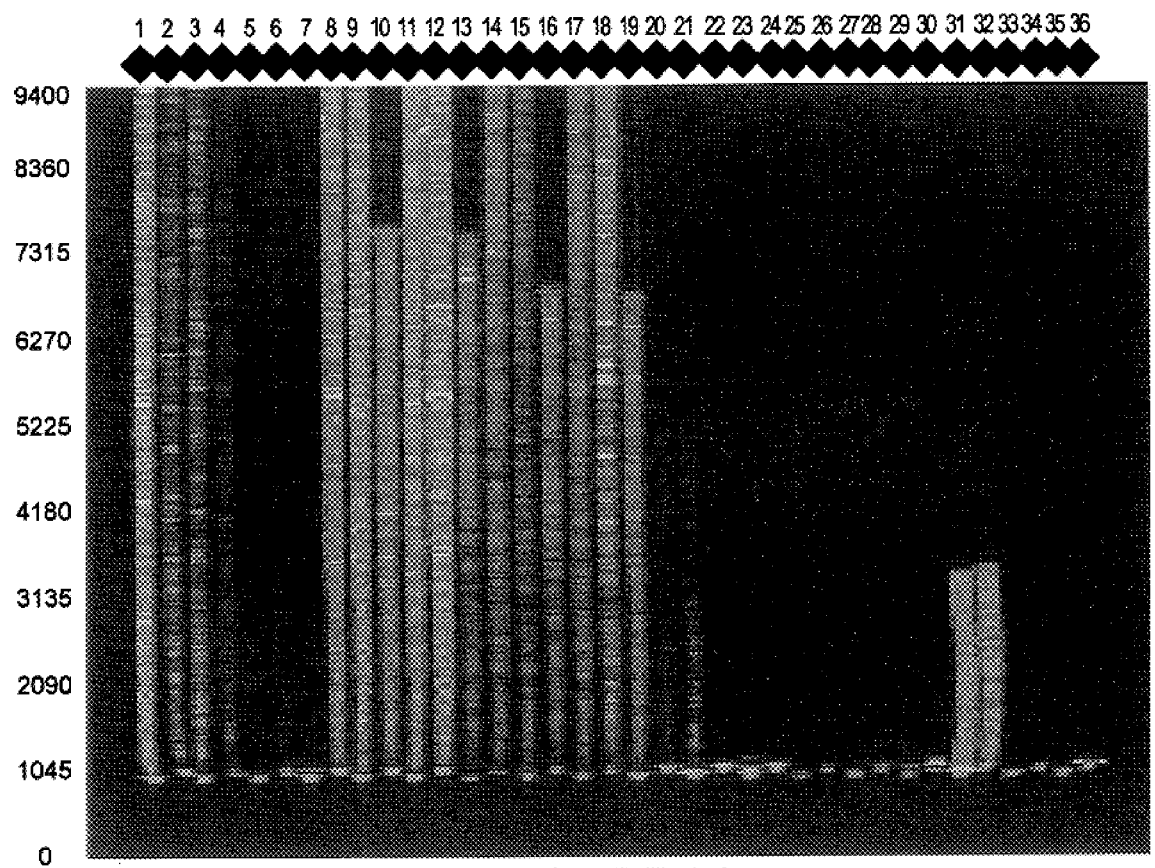
Figure 3B:
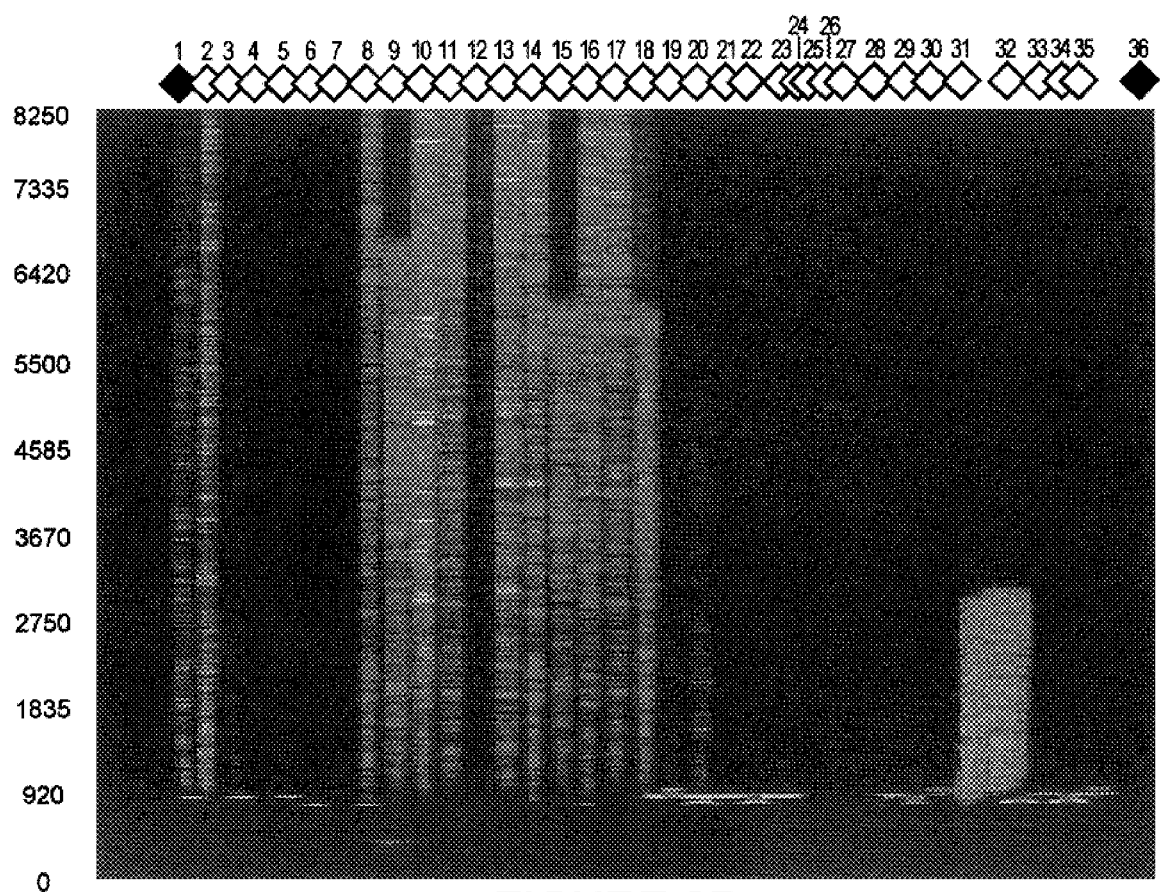
Figure 3C:
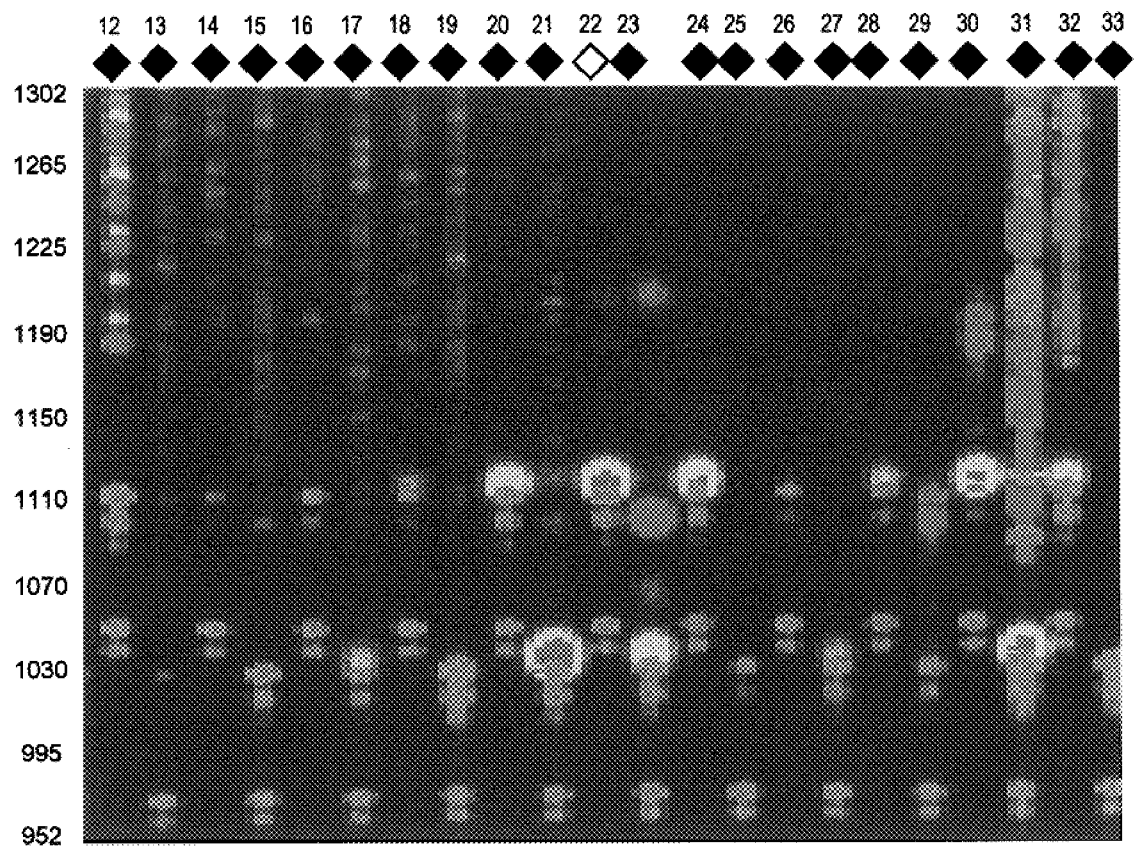

A DNA sequencing gel file from a PE Applied Biosystems Model 377 XL Automated DNA sequencer in which the samples were constituted in loading dye which contained the fluorogenic oligo according to the present invention is displayed in FIG. 3A. Each of the thirty-two lanes on the gel are clearly delineated by the "blue" oligo (at position 1045 on the ordinate), and the sequencer had no problems in correctly assigning lane positions. Note that in this set of samples, there were several "non-reactions" and that lanes 5, 6, 7, and 22–29 are otherwise blank, except for the presence of the blue oligo. FIG. 3B contains the DNA sequencing gel file from a PE Applied Biosystems Model 377 XL Automated DNA sequencer in which the identical samples shown in FIG. 3A were constituted in loading dye which DID NOT contain the fluorogenic oligo. Because of the large number of lanes which do not contain fluorogenic components, the sequencer INCORRECTLY assigned multiple lanes on the gel. If not for the presence of the fluorescent oligo, the information contained in this sample set would have been lost or misinterpreted. An enlargement of the region for sample Lanes 12–33 is shown in FIG. 3C, which illustrates the use of a fluorogenic oligo according to the present invention. Note that in the enlargement, the dyed oligo actually runs as a set of four bands in each lane, likely due to different structural conformations assumed by the oligo. Samples in odd numbered lanes are loaded and run for 5 minutes prior to loading samples into even numbered lanes. Hence, the "staggered" appearance to the movement of the fluorogenic oligo. In using the fluorogenic oligo, no errors in lane assignments were made even in the region of Lanes 22–29, which contain incomplete or failure reactions.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A marker to identify individual lanes on an electrophoresis gel run on an automated DNA sequencer, comprising the loading buffer used in the automated DNA sequencer;
a DNA sequencing sample; and
a lane-identifying marker DNA fragment labeled with a fluorophore, wherein the fluorophore is detectable by the DNA sequencer.

2. A marker according to claim 1, wherein the loading buffer further comprises a 5:1 ratio of deionized formamide and 50 mg/ml blue dextran in 25 mM EDTA, pH 8.0.

3. A marker according to claim 1, wherein the fluorophore is covalently attached to the DNA fragment.

4. A marker according to claim 3, wherein the fluorophore is attached to the DNA fragment at the 5' end of the DNA fragment.

5. A marker according to claim 3, wherein the fluorophore is attached to the DNA fragment at the 3' end of the DNA fragment.

6. A marker according to claim 1, wherein the fluorophore that labels the DNA fragment possesses a high quantum yield for fluorescence, well-resolved absorption and emission maxima, and causes minimal alteration in the electrophoretic mobility of the DNA to which it is attached.

7. A marker according to claim 1, wherein the fluorophore emits in the 500–700 nm wavelength range.

8. A marker according to claim 7, wherein the fluorophore is 6-FAM.

9. A marker according to claim 1, wherein the DNA fragment is a chemically synthesized oligonucleotide.

10. A marker to identify individual lanes on an electrophoresis gel run on an automated DNA sequencer, comprising the loading buffer used in the automated DNA sequencer;
a DNA sequencing sample; and
a lane-identifying marker DNA fragment labeled with a fluorophore, wherein the fluorophore is detectable by the DNA sequencer, and wherein the length of the DNA fragment is selected such that the labeled DNA fragment will enter the gel to a migration distance slightly longer than the migration distance of the first set of sequencing data from the sequencing reaction, such that inclusion of the marker DNA does not obstruct, interfere, or obscure any of the sequencing data.

11. A marker according to claim 10, wherein the loading buffer further comprises a 5:1 ratio of deionized formamide and 50 mg/ml blue dextran in 25 mM EDTA, pH 8.0.

12. A marker according to claim 10, wherein the fluorophore is covalently attached to the DNA fragment.

13. A marker according to claim 10, wherein the fluorophore is attached to the DNA fragment at the 5' end of the DNA fragment.

14. A marker according to claim 10, wherein the fluorophore is attached to the DNA fragment at the 3' end of the DNA fragment.

15. A marker according to claim 10, wherein the fluorophore that labels the DNA fragment possesses a high quantum yield for fluorescence, well-resolved absorption and emission maxima, and causes minimal alteration in the electrophoretic mobility of the DNA to which it is attached.

16. A marker according to claim 10, wherein the fluorophore emits in the 500–700 nm wavelength range.

17. A marker according to claim 16, wherein the fluorophore is 6-FAM.

18. A marker according to claim 10, wherein the DNA fragment is a chemically synthesized oligonucleotide.

19. A marker according to claim 10, wherein the DNA fragment is up to about 30 bases in length.

20. A marker according to claim 19, wherein the DNA fragment is about 17 to about 24 bases in length.

21. A marker according to claim 20, wherein the DNA fragment is 18 bases in length.

22. A marker according to claim 21, wherein the nucleotide sequence of the DNA fragment is TAATACGACT-CACTATAG (SEQ ID NO: 1).

23. A marker to identify individual lanes on an electrophoresis gel run on an automated DNA sequencer, comprising
    the loading buffer used in the automated DNA sequencer;
    a DNA sequencing sample; and
    a lane-identifying marker DNA fragment labeled with a fluorophore, wherein the fluorophore is detectable by the DNA sequencer, and has an emission maximum different than any of the nucleotide dyes.

24. A marker according to claim 23, wherein the loading buffer further comprises a 5:1 ratio of deionized formamide and 50 mg/ml blue dextran in 25 mM EDTA, pH 8.0.

25. A marker according to claim 23, wherein the fluorophore is covalently attached to the DNA fragment.

26. A marker according to claim 23, wherein the fluorophore is attached to the DNA fragment at the 5' end of the DNA fragment.

27. A marker according to claim 23, wherein the fluorophore is attached to the DNA fragment at the 3' end of the DNA fragment.

28. A marker according to claim 23, wherein the fluorophore that labels the DNA fragment possesses a high quantum yield for fluorescence, well-resolved absorption and emission maxima, and causes minimal alteration in the electrophoretic mobility of the DNA to which it is attached.

29. A marker according to claim 23, wherein the fluorophore emits in the 500–700 nm wavelength range.

30. A marker according to claim 23, wherein the DNA fragment is a chemically synthesized oligonucleotide.

31. A process for identifying individual lanes on an electrophoresis gel run on an automated DNA sequencer, comprising providing a loading buffer formulation for each sample to be run on the gel, wherein said buffer comprises a lane-identifying marker DNA fragment labeled with a fluorophore, wherein the fluorophore is detectable by the DNA sequencer.

32. A process according to claim 31, wherein the loading buffer comprising a labeled DNA fragment is loaded into every lane of the gel.

33. A process according to claim 31, wherein the loading buffer further comprises a 5:1 ratio of deionized formamide and 50 mg/ml blue dextran in 25 mM EDTA, pH 8.0.

34. A process according to claim 31, wherein the fluorophore is covalently attached to the DNA fragment.

35. A process according to claim 34, wherein the fluorophore is attached to the DNA fragment at the 5' end of the DNA fragment.

36. A process according to claim 34, wherein the fluorophore is attached to the DNA fragment at the 3' end of the DNA fragment.

37. A process according to claim 31, wherein the fluorophore that labels the DNA fragment possesses a high quantum yield for fluorescence, well-resolved absorption and emission maxima, and causes minimal alteration in the electrophoretic mobility of the DNA to which it is attached.

38. A process according to claim 31, wherein the fluorophore emits in the 500–700 nm wavelength range.

39. A process according to claim 38, wherein the fluorophore is 6-FAM.

40. A process according to claim 31, wherein the DNA fragment is a chemically synthesized oligonucleotide.

41. A process for identifying individual lanes on an electrophoresis gel run on an automated DNA sequencer, comprising providing a loading buffer formulation for each sample to be run on the gel, wherein said buffer comprises a marker comprising a lane-identifying marker DNA fragment labeled with a fluorophore, wherein the fluorophore is detectable by the DNA sequencer, and wherein the length of the DNA fragment is selected such that the labeled DNA fragment will enter the gel to a migration distance slightly longer than the migration distance of the first set of sequencing data from the sequencing reaction, such that inclusion of the marker DNA does not obstruct, interfere, or obscure any of the sequencing data.

42. A process according to claim 41, wherein the loading buffer comprising a labeled DNA fragment is loaded into every lane of the gel.

43. A process according to claim 41, wherein the loading buffer further comprises a 5:1 ratio of deionized formamide and 50 mg/ml blue dextran in 25 mM EDTA, pH 8.0.

44. A process according to claim 41, wherein the fluorophore is covalently attached to the DNA fragment.

45. A process according to claim 44, wherein the fluorophore is attached to the DNA fragment at the 5' end of the DNA fragment.

46. A process according to claim 44, wherein the fluorophore is attached to the DNA fragment at the 3' end of the DNA fragment.

47. A process according to claim 41, wherein the fluorophore that labels the DNA fragment possesses a high quantum yield for fluorescence, well-resolved absorption and emission maxima, and causes minimal alteration in the electrophoretic mobility of the DNA to which it is attached.

48. A process according to claim 41, wherein the fluorophore emits in the 500–700 nm wavelength range.

49. A process according to claim 41, wherein the fluorophore is 6-FAM.

50. A process according to claim 41, wherein the DNA fragment is a chemically synthesized oligonucleotide.

51. A process according to claim 41, wherein the DNA fragment is up to about 30 bases in length.

52. A process according to claim 51, wherein the DNA fragment is about 17 to about 24 bases in length.

53. A process according to claim 52, wherein the DNA fragment is 18 bases in length.

54. A process according to claim 53, wherein the nucleotide sequence of the DNA fragment is TAATACGACT-CACTATAG (SEQ ID NO: 1).

55. A process for identifying individual lanes on an electrophoresis gel run on an automated DNA sequencer, comprising providing a loading buffer formulation for each sample to be run on the gel, wherein said buffer comprises a marker comprising a lane-identifying marker DNA fragment labeled with a fluorophore, wherein the fluorophore is detectable by the DNA sequencer, and has an emission maximum different than any of the nucleotide dyes.

56. A process according to claim 55, wherein the loading buffer comprising a labeled DNA fragment is loaded into every lane of the gel.

57. A process according to claim 55, wherein the loading buffer further comprises a 5:1 ratio of deionized formamide and 50 mg/ml blue dextran in 25 mM EDTA, pH 8.0.

58. A process according to claim 55, wherein the fluorophore is covalently attached to the DNA fragment.

59. A process according to claim 55, wherein the fluorophore is attached to the DNA fragment at the 5' end of the DNA fragment.

60. A process according to claim 55, wherein the fluorophore is attached to the DNA fragment at the 3' end of the DNA fragment.

61. A process according to claim 55, wherein the fluorophore that labels the DNA fragment possesses a high quantum yield for fluorescence, well-resolved absorption and emission maxima, and causes minimal alteration in the electrophoretic mobility of the DNA to which it is attached.

62. A process according to claim 55, wherein the fluorophore emits in the 500–700 nm wavelength range.

63. A process according to claim 55, wherein the DNA fragment is a chemically synthesized oligonucleotide.

* * * * *